US008945572B2

(12) United States Patent
Chant et al.

(10) Patent No.: US 8,945,572 B2
(45) Date of Patent: Feb. 3, 2015

(54) METHODS AND COMPOSITIONS FOR THE DIAGNOSIS AND TREATMENT OF CANCER

(75) Inventors: John Chant, Millbrae, CA (US);
Anthony S. Guerrero, San Francisco, CA (US); Peter Haverty, San Francisco, CA (US); Cynthia Honchell, San Francisco, CA (US); Kenneth Jung, San Francisco, CA (US); Thomas Wu, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 902 days.

(21) Appl. No.: 12/300,156

(22) PCT Filed: May 11, 2007

(86) PCT No.: PCT/US2007/068737
§ 371 (c)(1),
(2), (4) Date: Mar. 17, 2009

(87) PCT Pub. No.: WO2007/134210
PCT Pub. Date: Nov. 22, 2007

(65) Prior Publication Data
US 2009/0311250 A1     Dec. 17, 2009

Related U.S. Application Data

(60) Provisional application No. 60/799,772, filed on May 12, 2006.

(51) Int. Cl.
*A61K 39/00*     (2006.01)
*C12Q 1/68*      (2006.01)

(52) U.S. Cl.
CPC ........ *C12Q 1/6886* (2013.01); *C12Q 2600/106* (2013.01)
USPC .................. 424/181.1; 424/178.1; 424/133.1; 435/6.14

(58) Field of Classification Search
USPC ........... 514/1.1; 435/6, 6.12, 6.14; 530/387.3; 424/130.1, 133.1, 172.1, 178.1, 181.1
See application file for complete search history.

(56) References Cited

U.S. PATENT DOCUMENTS

| | | | |
|---|---|---|---|
| 5,863,888 A | | 1/1999 | Dionne |
| 6,852,318 B1 * | | 2/2005 | Varner ..................... 424/130.1 |
| 2004/0137442 A1 | | 7/2004 | Slamon |
| 2004/0138442 A1 | | 7/2004 | Walke |
| 2004/0180002 A1 * | | 9/2004 | Young et al. ................ 424/1.49 |
| 2004/0197328 A1 * | | 10/2004 | Young et al. ............... 424/141.1 |
| 2004/0258693 A1 * | | 12/2004 | Young et al. ............... 424/155.1 |
| 2005/0244880 A1 * | | 11/2005 | Kallioniemi et al. ............ 435/6 |

FOREIGN PATENT DOCUMENTS

| | | |
|---|---|---|
| WO | WO 1999/44062 | 9/1999 |
| WO | 00/46343 | 8/2000 |
| WO | 03/024987 A1 | 3/2003 |
| WO | 2005/066211 A2 | 7/2005 |
| WO | WO 2005/115363 | 12/2005 |
| WO | 2006/110581 A2 | 10/2006 |
| WO | 2007/134210 A2 | 11/2007 |

OTHER PUBLICATIONS

Gura (Science, 1997, 278:1041-1042).*
Kaiser (Science, 2006, 313: 1370).*
Gura (Science, 1995, 270:575-577).*
Tockman et al (Cancer Res., 1992, 52:2711s-2718s).*
Pritzker (Clinical Chemistry, 2002, 48:1147-1150).*
Bai et al. (Cancer Res., 2010, 70: 7630-9).*
Otte et al. (European Journal of Clinical Investigation, 2000, 30, 222-229).*
Yoshino et al. (Oncology Reports 2005, 13: 247-252).*
Eswarakumar et al., "Cellular signaling by fibroblast growth factor receptors" Cytokine Growth Factor Rev. 16(2):139-49 (Apr. 2005).
Miki et al., "Determination of ligand-binding specificity by alternative splicing: two distinct growth factor receptors encoded by a single gene" Proc Natl Acad Sci U S A 89(1):246-50 (1992).
Matsuike et al., "Expression of fibroblast growth factor (FGF)-10 in human colorectal adenocarcinoma cells" J Nippon Med Sch. 68(5):397-404 (2001).
Watanabe et al., "Overexpression of keratinocyte growth factor in cancer cells and enterochromaffin cells in human colorectal cancer" Pathol Int. 50(5):363-72 (May 2000).
Al-Kuraya et al., "Prognostic relevance of gene amplifications and coamplifications in breast cancer" Cancer Res. 64(23):8534-40 (Dec. 2004).
Post et al., "Keratinocyte growth factor and its receptor are involved in regulating early lung branching" Development 122(10):3107-15 (Oct. 1996).
Katoh et al., "K-sam gene encodes secreted as well as transmembrane receptor tyrosine kinase" Proc Natl Acad Sci U S A. 89(7):2960-4 (Apr. 1992).
Takano et al, "Epidermal growth factor receptor gene mutations and increased copy numbers predict gefitinib sensitivity in patients with recurrent non-small-cell lung cancer" J Clin Oncol. 23(28):6829-37 (Oct. 2005).
Moffa et al., "Transforming potential of alternatively spliced variants of fibroblast growth factor receptor 2 in human mammary epithelial cells" Mol Cancer Res. 2(11):643-52 (Nov. 2004).
Bernard-Pierrot et al., "Inhibition of human bladder tumour cell growth by fibroblast growth factor receptor 2b is independent of its kinase activity. Involvement of the carboxy-terminal region of the receptor" Oncogene 23(57):9201-11 (Dec. 2004).

(Continued)

*Primary Examiner* — Mark Halvorson
*Assistant Examiner* — Yan Xiao
(74) *Attorney, Agent, or Firm* — Jessica Richardson; Alissa H. Faris; Arnold & Porter LLP

(57) ABSTRACT

Methods and compositions are provided for the diagnosis and treatment of colorectal cancers associated with amplification or overexpression of the FGFR2 gene.

2 Claims, 1 Drawing Sheet

(56) References Cited

OTHER PUBLICATIONS

Dionne et al., "Cloning and expression of two distinct high-affinity receptors cross-reacting with acidic and basic fibroblast growth factors" EMBO J. 9(9):2685-92 (1990).

Ornitz et al., "Receptor specificity of the fibroblast growth factor family" Journal of Biological Chemistry 271(25):15292-15297 (Jun. 21, 1996).

Dell and Williams, "A novel form of fibroblast growth factor receptor 2. Alternative splicing of the third immunoglobulin-like domain confers ligand binding specificity" Journal of Biological Chemistry 267(29):21225-21229 (Oct. 15, 1992).

Plotnikov et al., "Crystal structures of two FGF-FGFR complexes reveal the determinants of ligand-receptor specificity" Cell 101(4):413-24 (May 2000).

Hattori et al., "K-sam, an amplified gene in stomach cancer, is a member of the heparin-binding growth factor receptor genes" Proc Natl Acad Sci U S A 87(15):5983-7 (1990).

Zhao et al., "Homozygous deletions and chromosome amplifications in human lung carcinomas revealed by single nucleotide polymorphism array analysis" Cancer Res. 65(13):5561-70 (Jul. 2005).

Mohammadi et al., "Structures of the tyrosine kinase domain of fibroblast growth factor receptor in complex with inhibitors" Science 276:955-60 (May 1997).

Yamada et al., "Suppression of glioblastoma cell growth following antisense oligonucleotide-mediated inhibition of fibroblast growth factor receptor expression" Glia 28(1):66-76 (Oct. 1999).

Bottaro et al., "A keratinocyte growth factor receptor-derived peptide antagonist identifies part of the ligand binding site" J Biol Chem. 268(13):9180-3 (May 1993).

Edwards et al. "Gene amplifications associated with the development of hormone-resistant prostate cancer", Clinical Cancer Research 9:5271-5281, 2003.

Hattori et al. "Immunohistochemical detection of K-sam protein in stomach cancer", Clinical Cancer Research 2:1373-1381, 1996.

Kadota et al. "Identification of novel gene amplifications in breast cancer and coexistence of gene amplification with an activating mutation of PIK3CA", Cancer Research 69:7357-7365, 2009.

Tannheimer et al. "Characterization of fibroblast growth factor receptor 2 overexpression in the human breast cancer cell line SUM-52PE", Breast Cancer Research 2:311-320, 2000.

\* cited by examiner

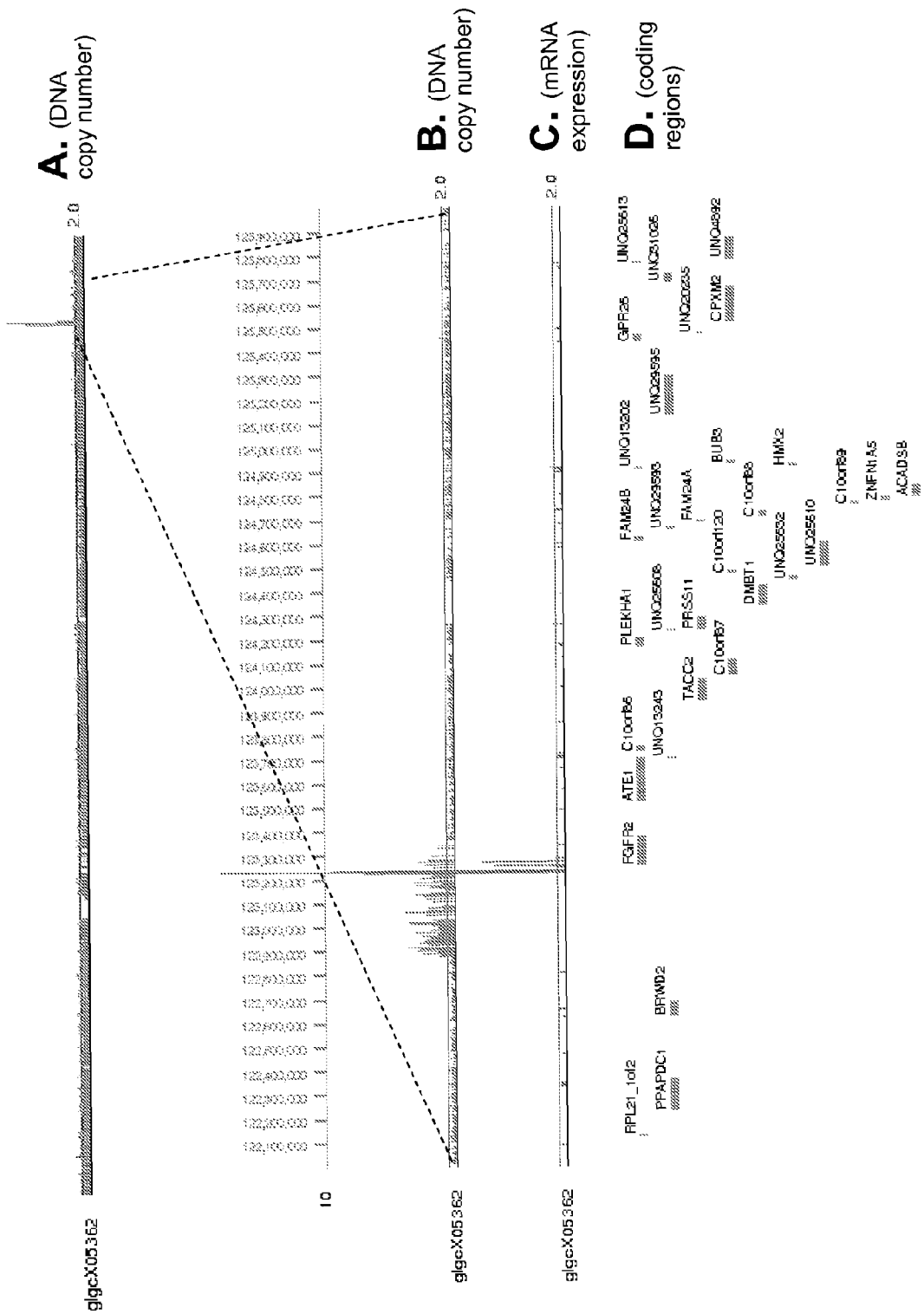

US 8,945,572 B2

METHODS AND COMPOSITIONS FOR THE DIAGNOSIS AND TREATMENT OF CANCER

This application is a US National Stage of PCT/US2007/068737, filed on May 11, 2007, which claims the benefit of U.S. Provisional Application 60/799,772, filed May 12, 2006. The entire disclosures of the foregoing applications are incorporated by reference herein.

REFERENCE TO A SEQUENCE LISTING

The instant application contains a Sequence Listing which has been submitted in ASCII format via EFS-Web and is hereby incorporated by reference in its entirety. Said ASCII copy, created on Nov. 8, 2008, is named P2364R1sequence.txt and is 14328 bytes in size.

FIELD OF THE INVENTION

The present invention relates to methods and compositions for the diagnosis and treatment of cancers associated with gene amplification.

BACKGROUND

Cancer is characterized by an increase in the number of abnormal, or neoplastic, cells derived from a normal tissue that proliferate and, under certain circumstances, invade adjacent tissues and eventually metastasize via the blood or lymphatic system. Alteration of gene expression is intimately related to uncontrolled cell growth and de-differentiation, which are common features of cancer. Certain cancers are characterized by overexpression of certain genes, e.g., oncogenes. A well known mechanism of gene overexpression in cancer cells is gene amplification. Gene amplification is a process in which multiple copies of one or more genes are produced in the chromosome of a cell. In certain instances, the process involves unscheduled replication of the region of the chromosome comprising those genes, followed by recombination of the replicated segments back into the chromosome (Alitalo et al., *Adv. Cancer Res.*, 47:235-281 [1986]). In certain cases, overexpression of a gene is correlated with gene amplification, i.e., is proportional to the number of copies made.

Amplification and/or overexpression of certain proto-oncogenes, e.g., those that encode growth factors and growth factor receptors, play important roles in the pathogenesis of various human malignancies. In certain instances, amplification and/or overexpression are associated with more malignant forms of cancer and thus may predict clinical outcome (Schwab et al., *Genes Chromosomes Cancer*, 1:181-193 [1990]; Alitalo et al., supra). For example, the human erbB2 gene (also known as her2 or c-erbB-2), which encodes a 185-kd transmembrane glycoprotein receptor (p185$^{HER2}$ or HER2) related to the epidermal growth factor receptor EGFR, is overexpressed in about 25% to 30% of human breast cancers (Slamon et al., *Science*, 235:177-182 [1987]; Slamon et al., *Science*, 244:707-712 [1989]). Overexpression of erbB2 is considered a predictor of a poor prognosis, especially in patients with primary disease that involves axillary lymph nodes (Slamon et al., [1987] and [1989], supra; Ravdin and Chamness, *Gene*, 159:19-27 [1995]; and Hynes and Stern, *Biochim. Biophys. Acta*, 1198:165-184 [1994]). Overexpression of erbB2 has also been linked to sensitivity and/or resistance to certain hormone therapy and chemotherapeutic regimens, including CMF (cyclophosphamide, methotrexate, and fluoruracil) and anthracyclines (Baselga et al., *Oncology*, 11 (3 Suppl 1):43-48 [1997]). However, patients that overexpress erbB2 show greater response to treatment with taxanes. Id.

Overexpression of erbB2 has provided the basis for targeted breast cancer therapies. A recombinant humanized anti-ErbB2 (anti-HER2) monoclonal antibody (Herceptin™, Genentech, Inc.) has been successfully used to treat patients with ErbB2-overexpressing metastatic breast cancer. (Baselga et al., *J. Clin. Oncol.*, 14:737-744 [1996]).

A continuing need exists for compositions and methods that target amplified genes and the products of those genes in the diagnosis and treatment of cancer.

A continuing need also exists for compositions and methods for the diagnosis and/or treatment of colorectal cancer. Over 56,000 people died of colorectal cancer in the year 2000. See Holen and Kemeny (2002) "Colorectal Cancer: Epidemiology and Treatment," in *Encyclopedia of Cancer*, vol. 2 (Elsevier Sciences, USA), pages 1-8. There are approximately 110,000 new cases of colon cancer diagnosed in the United States each year, accounting for approximately 15% of all cancer cases. Id. There are approximately 45,000 new cases of rectal cancer diagnosed in the United States each year, accounting for approximately 30% of all colorectal cancers. Id.

The invention described herein meets the above-described needs and provides other benefits.

SUMMARY

In one aspect, methods and compositions are provided for the diagnosis and treatment of colorectal cancers associated with amplification and/or overexpression of the FGFR2 gene.

In one aspect, a method of diagnosing the presence of a colorectal cancer in a mammal is provided, the method comprising detecting whether the FGFR2 gene is amplified in a test colorectal sample from the mammal relative to a control sample, wherein amplification of the FGFR2 gene indicates the presence of colorectal cancer in the mammal. In one embodiment, detecting whether the FGFR2 gene is amplified comprises detecting whether the copy number of the FGFR2 gene is increased by at least 5-fold.

In another aspect, a method of diagnosing the presence of a colorectal cancer in a mammal is provided, the method comprising detecting expression of the FGFR2 gene in a test colorectal sample from the mammal, wherein a higher level of FGFR2 gene expression in the test colorectal sample relative to a control sample indicates the presence of colorectal cancer in the mammal. In one embodiment, detecting expression of the FGFR2 gene comprises determining the level of mRNA transcription from the FGFR2 gene. In one embodiment, a higher level of FGFR2 expression comprises at least a 5-fold increase in mRNA transcription from the FGFR2 gene in the test colorectal sample relative to the control sample. In one embodiment, detecting expression of the FGFR2 gene comprises determining the level of FGFR2. In one embodiment, detecting expression of the FGFR2 gene comprises contacting the test colorectal sample with an anti-FGFR2 antibody and determining the level of expression of FGFR2 in the test colorectal sample by detecting binding of the anti-FGFR2 antibody to FGFR2. In one embodiment, a higher level of FGFR2 expression comprises at least a 5-fold increase in FGFR2 levels.

In another aspect, a method of inhibiting the proliferation of a colorectal cancer cell is provided, the method comprising exposing the cell to an FGFR2 antagonist. In one embodiment, the FGFR2 antagonist is an anti-FGFR2 antibody. In one embodiment, the anti-FGFR2 antibody binds to the extracellular domain of FGFR2. In one embodiment, the anti-FGFR2 antibody is an antibody fragment. In one embodiment, the anti-FGFR2 antibody is a chimeric or humanized antibody. In one embodiment, the anti-FGFR2 antibody is a human antibody. In one embodiment, the FGFR2 antagonist is an organic molecule that binds to FGFR2. In one embodiment, the FGFR2 antagonist is an oligopeptide that binds to FGFR2. In one embodiment, the FGFR2 antagonist is a soluble form of FGFR2. In one embodiment, the FGFR2 antagonist is an antisense nucleic acid of 10-30 nucleotides in length that binds to and reduces expression of a nucleic acid encoding FGFR2.

In another aspect, a method of inhibiting the proliferation of a colorectal cancer cell is provided, the method comprising exposing the cell to (a) a cytotoxic anti-FGFR2 antibody or (b) an immunoconjugate comprising an anti-FGFR2 antibody and a cytotoxic agent. In one embodiment, the method comprises exposing the cell to a cytotoxic anti-FGFR2 antibody. In one embodiment, the method comprises exposing the cell to an immunoconjugate comprising an anti-FGFR2 antibody and a cytotoxic agent. In one embodiment, the cytotoxic agent is a maytansinoid or an auristatin.

In another aspect, a method of treating a colorectal cancer associated with amplification or overexpression of the FGFR2 gene is provided, the method comprising administering to an individual having the colorectal cancer an effective amount of a pharmaceutical formulation comprising an antagonist of FGFR2. In one embodiment, the FGFR2 antagonist is an anti-FGFR2 antibody. In one embodiment, the anti-FGFR2 antibody binds to the extracellular domain of FGFR2. In one embodiment, the anti-FGFR2 antibody is an antibody fragment. In one embodiment, the anti-FGFR2 antibody is a chimeric or humanized antibody. In one embodiment, the anti-FGFR2 antibody is a human antibody. In one embodiment, the FGFR2 antagonist is an organic molecule that binds to FGFR2. In one embodiment, the FGFR2 antagonist is an oligopeptide that binds to FGFR2. In one embodiment, the FGFR2 antagonist is a soluble form of FGFR2. In one embodiment, the FGFR2 antagonist is an antisense nucleic acid of 10-30 nucleotides in length that binds to and reduces expression of a nucleic acid encoding FGFR2.

In another aspect, a method of treating a colorectal cancer associated with amplification or overexpression of the FGFR2 gene is provided, the method comprising administering to an individual having the colorectal cancer an effective amount of a pharmaceutical formulation comprising (a) a cytotoxic anti-FGFR2 antibody or (b) an immunoconjugate comprising an anti-FGFR2 antibody and a cytotoxic agent. In one embodiment, the method comprises administering to an individual having the colorectal cancer an effective amount of a pharmaceutical formulation comprising a cytotoxic anti-FGFR2 antibody. In one embodiment, the method comprises administering to an individual having the colorectal cancer an effective amount of a pharmaceutical formulation comprising an immunoconjugate comprising an anti-FGFR2 antibody and a cytotoxic agent. In one embodiment, the cytotoxic agent is a maytansinoid or an auristatin.

In another aspect, a method for determining whether an individual having a colorectal cancer will respond to a therapeutic that targets FGFR2 or the FGFR2 gene is provided, the method comprising determining whether the FGFR2 gene is amplified in the colorectal cancer, wherein amplification of the FGFR2 gene indicates that the individual will respond to the therapeutic. In one embodiment, the therapeutic is selected from (a) an FGFR2 antagonist, (b) a cytotoxic anti-FGFR2 antibody, or (c) an immunoconjugate comprising an anti-FGFR2 antibody and a cytotoxic agent.

BRIEF DESCRIPTION OF THE FIGURES

FIG. 1 shows the analysis of DNA copy number and mRNA expression for the FGFR2 gene in a particular colorectal tumor sample.

DETAILED DESCRIPTION OF EMBODIMENTS

Methods and compositions for the diagnosis and treatment of cancers associated with gene amplification are provided. In certain embodiments, the invention provides methods and compositions for the treatment of colorectal cancer associated with amplification and/or overexpression of the FGFR2 gene.

I. DEFINITIONS

The phrases "gene amplification" and "gene duplication" (and variants such as "amplification of a gene" or "duplication of a gene") are used interchangeably and refer to a process by which multiple copies of a gene or gene fragment are formed in a particular cell or cell line. The duplicated region (a stretch of amplified DNA) is often referred to as an "amplicon." Usually, the amount of the messenger RNA (mRNA) produced, i.e., the level of gene expression, also increases in proportion to the number of copies made of the particular gene.

The term "FGFR2," as used herein, refers to any native fibroblast growth factor receptor 2 from any vertebrate source, including mammals such as primates (e.g. humans and monkeys) and rodents (e.g., mice and rats), unless otherwise indicated. The term encompasses "full-length," unprocessed FGFR2 as well as any form of FGFR2 that results from processing in the cell. The term also encompasses naturally occurring variants of FGFR2, e.g., splice variants, allelic variants, and other isoforms. The term also encompasses fragments or variants of a native FGFR2 that maintain at least one biological activity of FGFR2.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "colorectal cancer" refers to any cancer of the large bowel, which includes the colon (the large intestine from the cecum to the rectum) and the rectum.

The term "neoplasm" or "neoplastic cell" refers to an abnormal tissue or cell that proliferates more rapidly than corresponding normal tissues or cells and continues to grow after removal of the stimulus that initiated the growth.

A "colorectal cancer cell" refers to a colon cancer cell or a rectal cancer cell, either in vivo or in vitro, and encompasses cell lines derived from colorectal cancer cells.

As used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

An "individual" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A "tumoricidal" agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxy-doxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXO- TERE® docetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylomithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell (such as a cell expressing FGFR2) either in vitro or in vivo. Thus, the growth inhibitory agent may be one which significantly reduces the percentage of cells (such as a cell expressing FGFR2) in S phase. Examples of growth inhibitory agents include agents that block cell cycle progression (at a place other than S phase), such as agents that induce GI arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

As used herein, the term "EGFR inhibitor" refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29):30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD 1839, gefitinib (IRESSA™) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluorophenyl)-N2-(1-methyl-piperidin-4-yl)-pyrimido[5,4-d] pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]6[5 [[[2methylsulfonyl)ethyl]amino] methyl]-2-furanyl]-4-quinazolinamine; Glaxo-SmithKline).

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC™, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo [2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC™); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone); or as described in any of the following patent publications: U.S. Pat. No. 5,804, 396; WO 1999/09016 (American Cyanamid); WO 1998/ 43960 (American Cyanamid); WO 1997/38983 (Warner Lambert); WO 1999/06378 (Warner Lambert); WO 1999/ 06396 (Warner Lambert); WO 1996/30347 (Pfizer, Inc); WO 1996/33978 (Zeneca); WO 1996/3397 (Zeneca); and WO 1996/33980 (Zeneca).

The term "antagonist" is used in the broadest sense, and includes any molecule that partially or fully blocks, inhibits, or neutralizes a biological activity of a polypeptide, such as FGFR2, or the transcription or translation thereof. Suitable antagonist molecules include, but are not limited to, antagonist antibodies, polypeptide fragments, oligopeptides, organic molecules (including small molecules), and antisense nucleic acids.

"Antibodies" (Abs) and "immunoglobulins" (Igs) refer to glycoproteins having similar structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The term "anti-FGFR2 antibody" or "an antibody that binds to FGFR2" refers to an antibody that is capable of binding FGFR2 with sufficient affinity such that the antibody is useful as a diagnostic and/or therapeutic agent in targeting FGFR2. Preferably, the extent of binding of an anti-FGFR2 antibody to an unrelated, non-FGFR2 protein is less than about 10% of the binding of the antibody to FGFR2 as measured, e.g., by a radioimmunoassay (RIA). In certain embodiments, an antibody that binds to FGFR2 has a dissociation constant (Kd) of $\leq 1$ μM, $\leq 100$ nM, $\leq 10$ nM, $\leq 1$ nM, or $\leq 0.1$ nM. In certain embodiments, an anti-FGFR2 antibody binds to an epitope of FGFR2 that is conserved among FGFR2 from different species.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example, one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is a minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO93/1161; Hudson et al. (2003) *Nat. Med.* 9:129-134; and Hollinger et al., Proc. Natl. Acad. Sci. USA 90: 6444-6448 (1993). Triabodies and tetrabodies are also described in Hudson et al. (2003) *Nat. Med.* 9:129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature*, 256: 495 (1975); Harlow et al., *Antibodies: A Laboratory Manual*, (Cold Spring Harbor Laboratory Press, $2^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132(2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; 5,661,016; Marks et al., *Bio. Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996) and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-

525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which comprises an amino acid sequence corresponding to that of an antibody produced by a human and/or has been made using any of the techniques for making human antibodies as disclosed herein. Such techniques include screening human-derived combinatorial libraries, such as phage display libraries (see, e.g., Marks et al., *J. Mol. Biol.*, 222: 581-597 (1991) and Hoogenboom et al., *Nucl. Acids Res.*, 19: 4133-4137 (1991)); using human myeloma and mouse-human heteromyeloma cell lines for the production of human monoclonal antibodies (see, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boemer et al., *J. Immunol.*, 147: 86 (1991)); and generating monoclonal antibodies in transgenic animals (e.g., mice) that are capable of producing a full repertoire of human antibodies in the absence of endogenous immunoglobulin production (see, e.g., Jakobovits et al., *Proc. Natl. Acad. Sci USA*, 90: 2551 (1993); Jakobovits et al., *Nature*, 362: 255 (1993); Bruggermann et al., *Year in Immunol.*, 7: 33 (1993)). This definition of a human antibody specifically excludes a humanized antibody comprising antigen-binding residues from a non-human animal.

An "affinity matured" antibody is one with one or more alterations in one or more CDRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of HVR and/or framework residues is described by: Barbas et al. *Proc Nat. Acad. Sci. USA* 91:3809-3813 (1994); Schieretal. *Gene* 169: 147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces a biological activity of the antigen it binds. Certain blocking antibodies or antagonist antibodies partially or completely inhibit the biological activity of the antigen.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known. Binding to human FcRn in vivo and serum half life of human FcRn high affinity binding polypeptides can be assayed, e.g., in transgenic mice or transfected human cell lines expressing human FcRn, or in primates administered with Fc variant polypeptides.

WO00/42072 (Presta) describes antibody variants with improved or diminished binding to FcRs. The content of that patent publication is specifically incorporated herein by reference. See, also, Shields et al. *J. Biol. Chem.* 9(2): 6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells and neutrophils. The effector cells may be isolated from a native source, e.g., from blood.

"Antibody-dependent cell-mediated cytotoxicity" or "ADCC" refers to a form of cytotoxicity in which immunoglobulin bound to Fc receptors (FcRs) present on certain cytotoxic effector cells (e.g. Natural Killer (NK) cells, neutrophils, and macrophages) enables those cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS (USA)* 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed.

Polypeptide variants with altered Fc region amino acid sequences and increased or decreased C1q binding capability are described in U.S. Pat. No. 6,194,551B1 and WO99/

51642. The contents of those patent publications are specifically incorporated herein by reference. See, also, Idusogie et al. *J. Immunol.* 164: 4178-4184 (2000).

The term "Fc region-comprising polypeptide" refers to a polypeptide, such as an antibody or immunoadhesin, which comprises an Fc region. The C-terminal lysine (residue 447 according to the EU numbering system) of the Fe region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

A "cytotoxic antibody" is an antibody that is capable of an effector function and/or inducing cell death upon binding to its target antigen.

An "immunoconjugate" refers to an antibody conjugated to one or more cytotoxic agents.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

A "small molecule" or "small organic molecule" is defined herein as an organic molecule having a molecular weight below about 500 Daltons.

An "FGFR2-binding oligopeptide" or an "oligopeptide that binds FGFR2" is an oligopeptide that is capable of binding FGFR2 with sufficient affinity such that the oligopeptide is useful as a diagnostic and/or therapeutic agent in targeting FGFR2. In certain embodiments, the extent of binding of an FGFR2-binding oligopeptide to an unrelated, non-FGFR2 protein is less than about 10% of the binding of the FGFR2-binding oligopeptide to FGFR2 as measured, e.g., by a surface plasmon resonance assay. In certain embodiments, an FGFR2-binding oligopeptide has a dissociation constant (Kd) of $\leq 1$ μM, $\leq 100$ nM, $\leq 10$ nM, $\leq 1$ nM, or $\leq 0.1$ nM.

An "FGFR2-binding organic molecule" or "an organic molecule that binds FGFR2" is an organic molecule other than an oligopeptide or antibody as defined herein that is capable of binding FGFR2 with sufficient affinity such that the organic molecule is useful as a diagnostic and/or therapeutic agent in targeting FGFR2. In certain embodiments, the extent of binding of an FGFR2-binding organic molecule to an unrelated, non-FGFR2 protein is less than about 10% of the binding of the FGFR2-binding organic molecule to FGFR2 as measured, e.g., by a surface plasmon resonance assay. In certain embodiments, an FGFR2-binding organic molecule has a dissociation constant (Kd) of $\leq 1$ μM, $\leq 100$ nM, $\leq 10$ nM, $\leq 1$ nM, or $\leq 0.1$ nM.

The dissociation constant (Kd) of any molecule that binds a target polypeptide may conveniently be measured using a surface plasmon resonance assay. Such assays may employ a BIAcore™-2000 or a BIAcore™-3000 (BIAcore, Inc., Piscataway, N.J.) at 25° C. with immobilized target polypeptide CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Target polypeptide is diluted with 10 mM sodium acetate, pH 4.8, to 5 μg/ml (~0.2 μM) before injection at a flow rate of 5 μl/minute to achieve approximately 10 response units (RU) of coupled protein. Following the injection of target polypeptide, 1 M ethanolamine is injected to block unreacted groups. For kinetics measurements, two-fold serial dilutions of the binding molecule (0.78 nM to 500 nM) are injected in PBS with 0.05% Tween 20 (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgrams. The equilibrium dissociation constant (Kd) is calculated as the ratio $k_{off}/k_{on}$. See, e.g., Chen, Y., et al., (1999) *J. Mol. Biol.* 293:865-881. If the on-rate of an antibody exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

A "liposome" is a small vesicle composed of various types of lipids, phospholipids and/or surfactant which is useful for delivery of an agent, e.g., a drug, to a mammal. The components of the liposome are commonly arranged in a bilayer formation, similar to the lipid arrangement of biological membranes.

The word "label" when used herein refers to a detectable compound or composition. The label may be detectable by itself (e.g., radioisotope labels or fluorescent labels) or, in the case of an enzymatic label, may catalyze chemical alteration of a substrate compound or composition which results in a detectable product. Radionuclides that can serve as detectable labels include, for example, I-131, I-123, I-125, Y-90, Re-188, Re-186, At-211, Cu-67, Bi-212, and Pd-109.

An "isolated" biological molecule, such as a nucleic acid, polypeptide, or antibody, is one which has been identified and separated and/or recovered from at least one component of its natural environment.

II. EMBODIMENTS OF THE INVENTION

Methods and compositions for the diagnosis and treatment of cancers associated with gene amplification are provided. In one aspect, methods and compositions for the diagnosis and treatment of colorectal cancer are provided. Those methods and compositions are based, in part, on the discovery that a region of chromosome 10 comprising the FGFR2 gene is amplified in a particular colorectal cancer, and this amplification is correlated with increased expression of FGFR2 mRNA.

FGFR2 is a member of the fibroblast growth factor receptor (FGFR) family of receptor protein tyrosine kinases, which also includes FGFR1, FGFR3, and FGFR4. Like other members of the FGFR family, FGFR2 contains an N-terminal extracellular ligand-binding domain, a single transmembrane domain, and a C-terminal cytoplasmic domain. The extracellular ligand-binding domain contains three immunoglobulin (Ig)-like domains; the second and third Ig-like domains are involved in ligand binding, as determined by X-ray crystallography studies. The cytoplasmic domain contains the catalytic protein tyrosine kinase core. For review, see, e.g., Eswarakumar et al. (2005) *Cytokine & Growth Factor Rev.* 16:139-149.

A full length, unprocessed form of human FGFR2 is shown in SEQ ID NO:1. That sequence contains the following features:

| Feature | Amino Acid Residues |
| --- | --- |
| Signal peptide | 1-21 |
| Predicted extracellular domain | 22-377 |
| First Ig-like domain | 39-125 |
| Second Ig-like domain | 154-247 |
| Third Ig-like domain | 256-358 |
| Predicted transmembrane domain | 378-398 |
| Predicted cytoplasmic domain | 399-821 |
| Protein tyrosine kinase domain | 481-770 |

Alternative splicing of FGFR2 mRNA generates various isoforms. Major isoforms include FGFR2b (also called KGFR in the scientific literature; SEQ ID NO:2 is representative of the human FGFR2b isoform); FGFR2c (also called BEK and FGFR2 in the scientific literature; SEQ ID NO:1 is representative of the human FGFR2c isoform); and an isoform called "K-SAM," which lacks the first Ig-like domain. See, e.g., Miki et al. (1992) *Proc. Natl Acad. Sci. USA* 89:246-250, and Dell et al. (1992) *J. Biol. Chem.* 267:21225-21229 (FGFR2b); Dionne et al. (1990) *EMBO J.* 9:2685-2692 (FGFR2c); and Hattori et al. (1990) *Proc. Natl. Acad. Sci. USA* 87:5983-5987 (K-SAM). The sequences of FGFR2b and FGFR2c are identical, except for a divergent 49-amino acid stretch spanning the second half of the third Ig-like domain. See Miki, supra. Accordingly, the features defined above for SEQ ID NO:1 also apply to SEQ ID NO:2. FGFR2b and FGFR2c show different ligand binding specificities, although both bind to fibroblast growth factor 1 (FGF1) with high affinity. See Ornitz et al. (1996) *J. Biol. Chem.* 271:15292-15297.

A. Methods of Diagnosis and Detection

In one aspect, methods of diagnosing colorectal cancer are provided. As described below in the Examples, a colorectal tumor was discovered in which a region of chromosome 10 was amplified. The only gene present within that amplified region is the FGFR2 gene, as shown in FIG. 1. (The chromosomal location of the FGFR2 gene is 10q26.) Thus, FGFR2 or the FGFR2 gene is an attractive target for colorectal cancer diagnostics and therapeutics.

Accordingly, in one aspect, a method of diagnosing the presence of a colorectal cancer in a mammal is provided, the method comprising detecting whether the FGFR2 gene is amplified in a test colorectal sample from the mammal relative to a control sample, wherein amplification of the FGFR2 gene indicates the presence of colorectal cancer in the mammal. As used herein, the term "detecting" encompasses quantitative or qualitative detection. A "test colorectal sample" is a biological sample derived from colorectal tissue that may or may not be cancerous, e.g., a sample of colorectal cells suspected of being cancerous or a whole cell extract or fractionated cell extract (such as a membrane preparation) derived from colorectal cells. A "control sample" is a biological sample derived from (a) normal tissue, e.g., normal colorectal cells or a whole cell extract or fractionated cell extract (such as a membrane preparation) derived from such cells, or (b) colorectal cancer tissue in which the FGFR2 gene is known not to be amplified or overexpressed, or a whole cell extract or fractionated cell extract derived therefrom. The FGFR2 gene is said to be "amplified" if the copy number of the FGFR2 gene is increased by at least 3-, 5-, 7-, 10-, 15-, 20-, 25-, 30-, 35-, 40-, 45-, or 50-fold in the test colorectal sample relative to the control sample.

In certain embodiments, detecting amplification of the FGFR2 gene is achieved using certain techniques known to those skilled in the art. For example, comparative genome hybridization may be used to produce a map of DNA sequence copy number as a function of chromosomal location. See, e.g., Kallioniemi et al. (1992) *Science* 258:818-821. Amplification of the FGFR2 gene may also be detected, e.g., by Southern hybridization using a probe specific for the FGFR2 gene or by real-time quantitative PCR.

In certain embodiments, detecting amplification of the FGFR2 gene is achieved by directly assessing the copy number of the FGFR2 gene, for example, by using a probe that hybridizes to the FGFR2 gene. In certain embodiments, detecting amplification of the FGFR2 gene is achieved by indirectly assessing the copy number of the FGFR2 gene, for example, by assessing the copy number of a chromosomal region that lies outside the FGFR2 gene but is co-amplified with the FGFR2 gene. Guidance for selecting such a region is provided, e.g., in FIG. 1, Panel C.

In another aspect, a method of diagnosing the presence of a colorectal cancer in a mammal is provided, the method comprising detecting expression of the FGFR2 gene in a test colorectal sample from the mammal, wherein a higher level of FGFR2 gene expression in the test colorectal sample relative to a control sample indicates the presence of colorectal cancer in the mammal. In certain embodiments, expression of the FGFR2 gene is detected by determining the level of mRNA transcription from the FGFR2 gene. Levels of mRNA transcription may be determined, either quantitatively or qualitatively, by various methods known to those skilled in the art. Levels of mRNA transcription may also be determined directly or indirectly by detecting levels of cDNA generated from the mRNA. Exemplary methods for determining levels of mRNA transcription include, but are not limited to, real-time quantitative RT-PCR and hybridization-based assays, including microarray-based assays and filter-based assays such as Northern blots. In certain embodiments, "a higher level of FGFR2 gene expression" means at least a 3-, 5-, 7-, 10-, 15-, 20-, 25-, 30-, 35-, 40-, 45-, or 50-fold increase in mRNA transcription from the FGFR2 gene.

In other embodiments, expression of the FGFR2 gene is detected by determining the level of FGFR2. Levels of FGFR2 may be determined, either quantitatively or quantitatively, by certain methods known to those skilled in the art, including antibody-based detection methods. In one embodiment, detecting expression of the FGFR2 gene in a test colorectal sample comprises contacting the test colorectal sample with an anti-FGFR2 antibody and determining the level of expression (either quantitatively or qualitatively) of FGFR2 in the test colorectal sample by detecting binding of the anti-FGFR2 antibody to FGFR2. In certain embodiments, binding of an anti-FGFR2 antibody to FGFR2 may be detected by various methods known to those skilled in the art including, but not limited to, fluorescence activated cell sorting, Western blot, radioimmunoassay, ELISA, and the like. In certain embodiments, "a higher level of FGFR2 gene expression" means at least a 3-, 5-, 7-, 10-, 15-, 20-, 25-, 30-, 35-, 40-, 45-, or 50-fold increase in FGFR2 levels.

For any of the above methods, the stated purpose of "diagnosing the presence of a colorectal cancer in a mammal" is nonlimiting and encompasses classifying the type of colorectal cancer present in a mammal by detecting whether the FGFR2 gene is amplified and/or expressed at a higher level in a test sample of colorectal cancer relative to a control sample. Classifying a colorectal cancer based on whether or not the FGFR2 gene is amplified and/or overexpressed is useful, e.g., for determining whether an individual having the colorectal cancer will respond to a therapeutic that targets FGFR2 or the FGFR2 gene, and thus, for selecting the optimal regimen for treating the colorectal cancer, as further described below. For example, a method is provided herein for determining whether an individual having colorectal cancer will respond to a therapeutic that targets FGFR2 or the FGFR2 gene, the method comprising determining whether the FGFR2 gene is amplified and/or overexpressed in the colorectal cancer (e.g., by using any of the methods described above), wherein amplification and/or overexpression of the FGFR2 gene indicates that the individual will respond to the therapeutic. A "therapeutic that targets FGFR2 or the FGFR2 gene" means any agent that affects the expression and/or an activity of FGFR2 or the FGFR2 gene including, but not limited to, any of the FGFR2 antagonists, cytotoxic antibodies, or immunoconjugates described below, Part B, including such therapeutics that are already known in the art as well as those that are later developed.

B. Compositions and Pharmaceutical Formulations

Pharmaceutical formulations for treating colorectal cancer are provided. In certain embodiments, a pharmaceutical formulation comprises at least one FGFR2 antagonist, a pharmaceutically acceptable carrier, and optionally, at least one additional therapeutic agent. In certain embodiments, an FGFR2 antagonist comprises an anti-FGFR2 antibody, an oligopeptide, an organic molecule, a soluble FGFR2 receptor, or an antisense nucleic acid. In certain embodiments, a pharmaceutical formulation comprises at least one cytotoxic anti-FGFR2 antibody, pharmaceutically acceptable carrier, and optionally, at least one additional therapeutic agent. In certain embodiments, a pharmaceutical formulation comprises at least one immunoconjugate, wherein the immunoconjugate comprises an antibody that binds FGFR2 and a cytotoxic agent; a pharmaceutically acceptable carrier; and optionally, at least one additional therapeutic agent.

1. FGFR2 Antagonists

In one aspect, an FGFR2 antagonist is an anti-FGFR2 antibody. In certain embodiments, an anti-FGFR2 antibody is a "blocking antibody," e.g, an antibody that fully or partially blocks the interaction of FGFR2 with its ligand. In certain embodiments, an anti-FGFR2 antibody binds to the extracellular domain of an FGFR2, e.g., a region within or overlapping amino acids 22-377 of SEQ ID NO:1 or SEQ ID NO:2. In certain embodiments, an anti-FGFR2 antibody binds to or otherwise occludes all or a portion of the ligand binding domain of an FGFR2. The ligand binding domain of FGFR2 has been examined by X-ray crystallography and includes the second and third Ig-like domains from about amino acid 154-247 and amino acid 256-358, respectively, of SEQ ID NO:1 or SEQ ID NO:2. See Part II, supra, and Plotnikov et al. (2000) *Cell* 101:413-424. Accordingly, in certain embodiments, an anti-FGFR2 antibody binds to or otherwise occludes all or a portion of the second or third Ig-like domain of an FGFR2.

In various embodiments of the invention, an anti-FGFR2 antibody (including antagonist anti-FGFR2 antibodies and cytotoxic anti-FGFR2 antibodies, discussed below, Part 2) is a monoclonal antibody. In various embodiments, an anti-FGFR2 antibody is an antibody fragment, e.g., a Fab, Fab'-SH, Fv, scFv, or (Fab')$_2$ fragment, or a single domain antibody (Domantis, Inc., Waltham, Mass.; see, e.g., U.S. Pat. No. 6,248,516 B1). In certain embodiments, an anti-FGFR2 antibody is a bispecific antibody (see, e.g., WO94/04690 and Suresh et al. (1986) *Methods in Enzymology* 121:210). In certain embodiments, an anti-FGFR2 antibody is a chimeric, humanized, or human antibody.

In another aspect, an FGFR2 antagonist is an oligopeptide that binds to an FGFR2. In one embodiment, an oligopeptide binds to the extracellular domain of an FGFR2. In one such embodiment, an oligopeptide binds to or otherwise occludes a region of the ligand binding domain, e.g., by binding to all or a portion of the second and/or third Ig-like domain. In another embodiment, an oligopeptide binds to the protein tyrosine kinase domain of an FGFR2 and/or reduces the activity of the protein tyrosine kinase domain of an FGFR2.

The above oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length. Such oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750, 373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. USA*, 81:3998-4002 (1984); Geysen et al., *Proc. Natl. Acad. Sci. USA*, 82:178-182 (1985); Geysen et al., in *Synthetic Peptides as Antigens*, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668). In certain embodiments, an oligopeptide may be conjugated to a cytotoxic agent.

In yet another aspect, an FGFR2 antagonist is an organic molecule that binds to FGFR2, other than an oligopeptide or antibody as described herein. An organic molecule may be, for example, a small molecule. In one embodiment, an organic molecule binds to the extracellular domain of an FGFR2. In one such embodiment, an organic molecule binds to or otherwise occludes a region of the ligand binding domain, e.g., by binding to all or a portion of the second and/or third Ig-like domain. In another embodiment, an organic molecule binds to the protein tyrosine kinase domain and/or reduces the activity of the protein tyrosine kinase domain of an FGFR2.

An organic molecule that binds to FGFR2 may be identified and chemically synthesized using known methodology (see, e.g., PCT Publication Nos. WO00/00823 and WO00/39585). Such organic molecules are usually less than about 2000 daltons in size, alternatively less than about 1500, 750, 500, 250 or 200 daltons in size, wherein such organic molecules that are capable of binding to FGFR2 may be identified without undue experimentation using well known techniques.

In this regard, it is noted that techniques for screening organic molecule libraries for molecules that are capable of binding to a polypeptide target are well known in the art (see, e.g., PCT Publication Nos. WO00/00823 and WO00/39585). In certain embodiments, an organic molecule may be conjugated to a cytotoxic agent.

Certain small molecule antagonists that bind to FGFR2 and inhibit the protein tyrosine kinase activity of FGFR2 are known in the art. Such molecules include, e.g., 1-tert-butyl-3-[6-(3,5-dimethoxy-phenyl)-2-(4-diethylamino-butylamino)-pyrido[2,3-d]pyrimidin-7-yl]-urea ("PD173074") (see, e.g., Moffa et al. (2004) Mol. Cancer Res. 2:643-652); and 3-[3-(2-carboxyethyl)-4-methylpyrrol-2-methylidenyl]-2-indolinone ("SU5402," Calbiochem) (see, e.g., Bernard-Pierrot (2004) Oncogene 23:9201-9211. Indolinones are a class of small molecules known to inhibit the receptor protein tyrosine kinase activity of FGFRs. See Mohammadi et al. (1997) 276:9555-960. In certain embodiments, an FGFR2 antagonist is a tyrosine kinase inhibitor, as defined herein.

In yet another aspect, an FGFR2 antagonist is a soluble form of FGFR2, i.e., a form of FGFR2 that is not anchored to the plasma membrane. Such soluble forms of FGFR2 may compete with membrane-bound FGFR2 for binding to an FGFR2 ligand. In certain embodiments, a soluble form of FGFR2 may comprise all or a ligand-binding portion of an extracellular domain of FGFR2, e.g., all or a ligand-binding portion of a polypeptide comprising amino acids 22-377 of SEQ ID NO:1 or SEQ ID NO:2. In certain embodiments, a soluble form of FGFR2 may comprise all or a ligand-binding portion of one or more ligand binding domains of FGFR2, e.g., all or a ligand-binding portion of a polypeptide comprising amino acids 154-247 and/or amino acids 256-368 of SEQ ID NO:1 or SEQ ID NO:2. In any of the above embodiments, a soluble form of FGFR2 may or may not further comprise a protein tyrosine kinase domain.

Naturally occurring, soluble forms of FGFR2 are reported in Katoh et al. (1992) Proc. Natl Acad. Sci. USA 89:2960-2964. Such forms include secreted forms of FGFR2 that either possess or lack a protein tyrosine kinase domain. Id. Additionally, two oligopeptides have been shown to be effective in competing with a membrane-bound isoform of FGFR2 (FGFR2b) for ligand binding. Bottaro et al. (1993) J. Biol. Chem. 268:9180-9183. Those peptides correspond to a 20- and 25-amino acid stretch, respectively, that spans a portion of one of the ligand binding domains (the third immunoglobulin-like domain). Thus, soluble forms of FGFR2 are well within the skill in the art.

In yet another aspect, an FGFR2 antagonist is an antisense nucleic acid that decreases expression of the FGFR2 gene (i.e., that decreases transcription of the FGFR2 gene and/or translation of FGFR2 mRNA). In certain embodiments, an antisense nucleic acid binds to a nucleic acid (DNA or RNA) encoding FGFR2. In certain embodiments, an antisense nucleic acid is an oligonucleotide of about 10-30 nucleotides in length (including all points between those endpoints). In certain embodiments, an antisense oligonucleotide comprises a modified sugar-phosphodiester backbones (or other sugar linkages, including phosphorothioate linkages and linkages as described in WO 91/06629), wherein such modified sugar-phosphodiester backbones are resistant to endogenous nucleases. In one embodiment, an antisense nucleic acid is an oligodeoxyribonucleotide, which results in the degradation and/or reduced transcription or translation of FGFR2 mRNA. Certain examples of FGFR2-specific antisense nucleic acids are known to those skilled in the art and are described, e.g., in the following publications: Post et al. (1996) Development 122:3107-3115 (describing a phosphorothioate oligodeoxyribonucleotide (15-mer) spanning the translational start site and two isoform-specific phosphorothioate oligodeoxyribonucleotides (16- and 19-mers)); Yamada et al. (1999) Glia 28:66-76 (describing a phosphorothioate oligodeoxyribonucleotide complementary to the translational start site); and WO03/024987 (describing phosphorothioate oligodeoxyribonucleotide (20-mers) targeting various regions of FGFR2 mRNA).

In certain embodiments, an antisense nucleic acid is an RNA that reduces expression of a target nucleic acid by "RNA interference" ("RNAi"). For review of RNAi, see, e.g., Novina et al. (2004) Nature 430:161-164. Such RNAs are derived from, for example, short interfering RNAs (siRNAs) and microRNAs. siRNAs, e.g., may be synthesized as double stranded oligoribonucleotides of about 18-26 nucleotides in length. Id. Thus, antisense nucleic acids that decrease expression of FGFR2 are well within the skill in the art.

2. Cytotoxic Antibodies

In one aspect, cytotoxic antibodies are provided. In certain embodiments, a cytotoxic antibody is an anti-FGFR2 antibody, such as those provided above, which effects an effector function and/or induces cell death. In certain embodiments, a cytotoxic anti-FGFR2 antibody binds to the extracellular domain of an FGFR2, e.g., a region within amino acids 22-377 of SEQ ID NO:1 or SEQ ID NO:2.

3. Immunoconjugates

Immunoconjugates, or "antibody-drug conjugates," are useful for the local delivery of cytotoxic agents in the treatment of cancer. See, e.g., Syrigos et al. (1999) Anticancer Research 19:605-614; Niculescu-Duvaz et al. (1997) Adv. Drug Deliv. Rev. 26:151-172; U.S. Pat. No. 4,975,278. Immunoconjugates allow for the targeted delivery of a drug moiety to a tumor, whereas systemic administration of unconjugated cytotoxic agents may result in unacceptable levels of toxicity to normal cells as well as the tumor cells sought to be eliminated. See Baldwin et al. (Mar. 15, 1986) Lancet pp. 603-05; Thorpe (1985) "Antibody Carriers Of Cytotoxic Agents In Cancer Therapy: A Review," in Monoclonal Antibodies '84: Biological and Clinical Applications (A. Pinchera et al., eds.) pp. 475-506.

In one aspect, an immunoconjugate comprises an antibody that binds FGFR2 (or an extracellular domain thereof), such as those provided above, and a cytotoxic agent, such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent may be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Maytansine and Maytansinoids

In one embodiment, an immunoconjugate comprises an anti-FGFR2 antibody conjugated to one or more maytansinoid molecules. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151, 042). Synthetic maytansinol and derivatives and analogues thereof are disclosed, for example, in U.S. Pat. Nos. 4,137, 230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

In an attempt to improve their therapeutic index, maytansine and maytansinoids have been conjugated to antibodies that bind to antigens on the surface of tumor cells. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM 1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) described immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-FGFR2 antibody-maytansinoid conjugates are prepared by chemically linking an anti-FGFR2 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin per antibody would be expected to enhance cytotoxicity over the use of naked antibody. Maytansinoids are well known in the art and can be synthesized using known techniques or isolated from natural sources. Suitable maytansinoids are disclosed, for example, in U.S. Pat. No. 5,208, 020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disufide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Certain coupling agents, including N-succinimidyl-3-(2-pyridyldithio) propionate (SPDP) (Carlsson et al., *Biochem. J.* 173:723-737 [1978]) and N-succinimidyl-4-(2-pyridylthio) pentanoate (SPP), provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolastatins

In some embodiments, an immunoconjugate comprises an anti-FGFR2 antibody conjugated to a dolastatin or dolostatin peptidic analog or derivative, e.g., an auristatin (U.S. Pat. Nos. 5,635,483; 5,780,588). Dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," US Patent Application Publication No.

US 2005-0238649 A1, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis,* 1996, 719-725; and Pettit et al (1996) *J. Chem. Soc. Perkin Trans.* 1 5:859-863. See also Doronina (2003) *Nat. Biotechnol.* 21(7):778-784; US Patent Application Publication No. 2005-0238649 A1, hereby incorporated by reference in its entirety (disclosing, e.g., linkers and methods of preparing monomethylvaline compounds such as MMAE and MMAF conjugated to linkers).

Calicheamicin

Another immunoconjugate of interest comprises an anti-FGFR2 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I, \gamma_2^I, \gamma_3^I$, N-acetyl-$\gamma_1^I$, PSAG and $\theta^I_1$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug to which the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to an anti-FGFR2 antibody include BCNU, streptozoicin, vincristine and 5-fluorouracil, the family of agents known collectively as LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

In another aspect, an immunoconjugate may comprise an anti-FGFR2 antibody and a compound with nucleolytic activity (e.g., a ribonuclease or a DNA endonuclease such as a deoxyribonuclease; DNase).

For selective destruction of a tumor, an immunoconjugate may comprise an anti-FGFR2 antibody and a highly radioactive atom. A variety of radioactive isotopes are available for the production of radioconjugated anti-FGFR2 antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the immunoconjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes other methods in detail.

Conjugates of an antibody and one or more small molecule toxins, such as a calicheamicin, maytansinoids, a trichothene, and CC1065, and the derivatives of these toxins that have toxin activity, are also contemplated herein.

4. Additional Therapeutic Agents

Pharmaceutical formulations may optionally comprise at least one additional therapeutic agent (i.e., in addition to an FGFR2 antagonist, cytotoxic antibody, or immunoconjugate). Such additional therapeutic agents are described in further detail below, Part C.

5. Preparation of Pharmaceutical Formulations

Pharmaceutical formulations comprising any of the above agents are prepared for storage by mixing the antibody or immunoconjugate having the desired degree of purity with optional physiologically acceptable carriers, excipients or stabilizers (*Remington's Pharmaceutical Sciences* 16th edition, Osol, A. Ed. (1980)) in the form of aqueous solutions or lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride); phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutical formulations to be used for in vivo administration are generally sterile. This is readily accomplished by filtration through sterile filtration membranes.

An agent may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the agent of interest, which matrices are in the form of shaped articles, e.g., films, or microcapsule. Examples of sustained-release matrices include polyesters, hydrogel (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogel release proteins for shorter time periods. When encapsulated agents remain in the body for a long time, they may denature or aggregate as a result of exposure to moisture at 37° C., resulting in a loss of biological activity and, for antibodies, possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

C. Methods of Treatment and Related Methods

Therapeutic methods using an FGFR2 antagonist, a cytotoxic antibody, or an immunoconjugate are provided. Such methods include in vitro, ex vivo, and/or in vivo therapeutic methods, unless otherwise indicated.

In one aspect, the invention provides a method of inhibiting the proliferation of a colorectal cancer cell, the method comprising exposing the cell to 1) an FGFR2 antagonist, 2) a cytotoxic anti-FGFR2 antibody, or 3) an immunoconjugate comprising an anti-FGFR2 antibody and a cytotoxic agent. In certain embodiments, the FGFR2 gene is amplified or overexpressed in the colorectal cancer cell. In certain embodiments, the colorectal cancer cell is derived from a colorectal tumor, e.g., a colorectal tumor in which the FGFR2 gene is amplified or overexpressed. In certain embodiments, the colorectal cancer cell may be of any of the following cell lines: C70, HT29, LIM1863, SW1417, SW403, SW480, SW620, SW837, VACO4A, DLD-1, GP2d, HCA7, HCT-15, HCT116, LoVo, LS174T, LS411, VACO5, VACO400, or VACO429. "Inhibiting the proliferation" means decreasing a cell's proliferation by at least 10%, 20%, 30%, 40%, 50%, 60%, 70%, 80%, 90%, 95%, or 100%, and includes inducing cell death.

Inhibition of cell proliferation may be measured using methods known to those skilled in the art. For example, a convenient assay for measuring cell proliferation is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) *J. Immunol. Meth.* 160:81-88, U.S. Pat. No. 6,602,677. The assay may be conducted in 96- or 384-well format, making it amenable to automated high-throughput screening (HTS). See Cree et al (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, a method of treating a colorectal cancer is provided, the method comprising administering to an individual having the colorectal cancer an effective amount of a pharmaceutical formulation comprising 1) an FGFR2 antagonist, 2) a cytotoxic anti-FGFR2 antibody, or 3) an immunoconjugate comprising an anti-FGFR2 antibody and a cytotoxic agent. In certain embodiments, the colorectal cancer is associated with amplification or overexpression of the FGFR2 gene. In certain embodiments, the individual is a non-human animal model for colorectal cancer. Mouse models of colorectal cancer are discussed in detail in Heijstek et al. (2005) *Dig. Surg.* 22:16-25. In certain embodiments, the individual is a human. In certain embodiments, an effective amount of the pharmaceutical formulation results in any one of the following: reduction in the number of cancer cells or elimination of the cancer cells; reduction in the tumor size; full or partial inhibition of cancer cell infiltration into peripheral organs, including the spread of cancer into soft tissue and bone; full or partial inhibition of tumor metastasis; full or partial inhibition of tumor growth; and/or full or partial relief of one or more of the symptoms associated with the cancer; and reduced morbidity and mortality.

In certain embodiments, a pharmaceutical formulation comprising 1) an FGFR2 antagonist, 2) a cytotoxic anti-FGFR2 antibody, or 3) an immunoconjugate comprising an anti-FGFR2 antibody and a cytotoxic agent is administered in combination with at least one additional therapeutic agent and/or adjuvant. In certain embodiments, an additional therapeutic agent is a cytotoxic agent, a chemotherapeutic agent, or a growth inhibitory agent. In one of such embodiments, a chemotherapeutic agent is an agent or a combination of agents used in the treatment of colorectal cancer. Such agents include, but are not limited to, fluorouracil (5FU) alone or in combination with leucovorin or levamisole; edrocolomab; irinotecan; oxaliplatin; raltitrexed; and fluoropyrimidines.

Such combination therapies noted above encompass combined administration (where two or more therapeutic agents are included in the same or separate formulations), and separate administration, in which case, administration of an FGFR2 antagonist, cytotoxic antibody, or immunoconjugate can occur prior to, simultaneously, and/or following, administration of the additional therapeutic agent and/or adjuvant. An FGFR2 antagonist, cytotoxic antibody, or immunoconjugate can also be used in combination with radiation therapy.

An FGFR2 antagonist, cytotoxic antibody, or immunoconjugate (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the FGFR2 antagonist, cytotoxic antibody, or immunoconjugate is suitably administered by pulse infusion, particularly with declining doses of the FGFR2 antagonist, cytotoxic antibody, or immunoconjugate.

Dosing can be by any suitable route, e.g. by injections, such as intravenous or subcutaneous injections, depending in part on whether the administration is brief or chronic.

Where the FGFR2 antagonist is an antisense nucleic acid, guidance for dosage and in vivo administration of antisense nucleic acids may be found in Khan et al. (2004) *J. Drug Targeting* 12:393-404.

Where the therapeutic agent is an anti-FGFR2 antibody or immunoconjugate thereof, the appropriate dosage of the antibody or immunoconjugate (when used alone or in combination with one or more other additional therapeutic agents, such as chemotherapeutic agents) will depend on the particular antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 μg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of an antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or, e.g., about six doses of the antibody or immunoconjugate). An initial higher loading dose, followed by one or more lower doses may be administered. An exemplary dosing regimen comprises administering an initial loading dose of about 4 mg/kg, followed by a weekly maintenance dose of about 2 mg/kg of the antibody or immunoconjugate. However, other dosage regimens may be useful.

III. EXAMPLES

A. Samples

Thirty fresh frozen colorectal tumors, each from a different patient sample, were selected for analysis. Each tumor sample had greater than 75% neoplastic cell content, as estimated by a pathologist. From each tumor both RNA and DNA were extracted and purified by standard methods.

B. DNA Copy Number Analysis

The GeneChip® Human Mapping 500K Array Set (Affymetrix, Santa Clara, Calif.) was used to measure DNA copy number changes in the thirty colorectal tumors. The Gene Chip® Human Mapping 500K Array Set consists of two arrays (the 250K "Sty I" array and the 250K "Nsp I" array), each containing probes specific for approximately 250,000 SNPs, for a total of approximately 500,000 SNPs. The SNPs are distributed throughout the genome, thereby permitting a genome-wide analysis of DNA copy number. Each array in the array set includes more than 6.5 million features, with each feature consisting of over 1 million copies of a 25-bp oligonucleotide of defined sequence.

From each tumor sample, DNA was amplified, labeled, and digested with either Sty 1 or Nsp 1 as per Affymetrix's standard protocols, and the resulting preparation was allowed to hybridize to both arrays of the GeneChip® Human Mapping 500K Array Set.

Hybridization to the microarrays was detected according to Affymetrix's standard protocols, and intensity values for each feature were generated. Intensity values were normalized to a reference set of normal genomic DNA. Features were then mapped to the human genome. Thus, the normalized intensity values reflected the DNA copy number at a particular genomic locus.

C. Expression Analysis

The GeneChip® Human Genome U133A 2.0 Array and the GeneChip® Human Genome U133 Plus 2.0 Array (Affymetrix, Santa Clara, Calif.) were used to measure relative mRNA expression in the thirty colorectal tumors. Purified RNA samples were reverse transcribed, amplified, labeled and otherwise treated as per Affymetrix's standard protocols and allowed to hybridize to one or the other of the arrays. Hybridization to the arrays was detected according to Affymetrix's standard methods, and intensity values for each feature were generated. The intensity value for each feature was normalized to the median intensity of that feature across all tumor samples. Features were then mapped to the corresponding coding regions in the genome. Thus, the normalized intensity values reflected mRNA expression levels for each feature, and each feature was correlated with a particular position in the genome.

D. Analysis and Results

One of the thirty colorectal tumor samples (designated glgcX05362) displayed a gene amplification and expression profile as shown in FIG. 1. In Panel A of that figure, the normalized intensity value from the DNA copy number analysis (Part B, above) for each feature is represented as a vertical line. The vertical lines are plotted along the horizontal axis in Panel A, which represents the length of chromosome 10. The height of each vertical line reflects the normalized intensity value, which is a measure of the DNA copy number at that point on the chromosome. A spike of signal intensity was observed near the right end of the chromosome.

Panel B shows an enlargement of the right end of chromosome 10 from 121,000,000 nucleotides to 126,000,000 nucleotides. As for Panel A, normalized intensity values from the DNA copy number analysis are shown as vertical lines. A cluster of normalized intensity values within that region of chromosome 10 showed about a 10-fold increase in copy number.

In Panel C, normalized intensity values from the expression analysis (Part C, above) are shown as vertical lines. The horizontal axis represents the same chromosomal region as in Panel B. Thus, the vertical lines in Panel C show the relative levels of mRNA expression from the coding regions within that chromosomal region. The height of each vertical line reflects the relative mRNA expression level for each feature.

Panel D shows the coding regions of genes known to map to the region of chromosome 10 depicted in Panels B and C.

Comparison of Panels B, C, and D, shows that only one gene, the FGFR2 gene, is present within the region of increased copy number observed in Panel B. The increase in DNA copy number of the FGFR2 gene is correlated with marked overexpression (at least about 10-40 fold overexpression) of the FGFR2 transcript, as shown in Panel C.

The high level amplification of the FGFR2 gene suggests that an increase in copy number of that gene causes overexpression of the encoded growth factor receptor, thereby promoting the growth and proliferation of colorectal tumor cells. The observed overexpression of FGFR2 mRNA is consistent with that conclusion.

Although the foregoing invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

What is claimed is:

1. A method of treating a colorectal cancer associated with amplification of the FGFR2 gene in an individual having the colorectal cancer, the method comprising i) determining whether the FGFR2 gene is amplified in the colorectal cancer, wherein amplification of the FGFR2 gene indicates that the individual will respond to the therapeutic, and ii) administering to said individual having the colorectal cancer associated with amplification of the FGFR2 gene, an effective amount of a pharmaceutical formulation comprising an immunoconjugate comprising an anti-FGFR2 antibody and a cytotoxic agent.

2. The method of claim 1, wherein the cytotoxic agent is a maytansinoid or an auristatin.

* * * * *

```
                          SEQUENCE LISTING

<160> NUMBER OF SEQ ID NOS: 2

<210> SEQ ID NO 1
<211> LENGTH: 821
<212> TYPE: PRT
<213> ORGANISM: Homo sapiens

<400> SEQUENCE: 1

Met Val Ser Trp Gly Arg Phe Ile Cys Leu Val Val Thr Met
 1               5                  10                  15

Ala Thr Leu Ser Leu Ala Arg Pro Ser Phe Ser Leu Val Glu Asp
                20                  25                  30

Thr Thr Leu Glu Pro Glu Glu Pro Pro Thr Lys Tyr Gln Ile Ser
                35                  40                  45

Gln Pro Glu Val Tyr Val Ala Ala Pro Gly Glu Ser Leu Glu Val
                50                  55                  60

Arg Cys Leu Leu Lys Asp Ala Ala Val Ile Ser Trp Thr Lys Asp
                65                  70                  75

Gly Val His Leu Gly Pro Asn Asn Arg Thr Val Leu Ile Gly Glu
                80                  85                  90

Tyr Leu Gln Ile Lys Gly Ala Thr Pro Arg Asp Ser Gly Leu Tyr
                95                  100                 105

Ala Cys Thr Ala Ser Arg Thr Val Asp Ser Glu Thr Trp Tyr Phe
                110                 115                 120

Met Val Asn Val Thr Asp Ala Ile Ser Ser Gly Asp Asp Glu Asp
                125                 130                 135

Asp Thr Asp Gly Ala Glu Asp Phe Val Ser Glu Asn Ser Asn Asn
                140                 145                 150

Lys Arg Ala Pro Tyr Trp Thr Asn Thr Glu Lys Met Glu Lys Arg
                155                 160                 165

Leu His Ala Val Pro Ala Ala Asn Thr Val Lys Phe Arg Cys Pro
                170                 175                 180

Ala Gly Gly Asn Pro Met Pro Thr Met Arg Trp Leu Lys Asn Gly
                185                 190                 195

Lys Glu Phe Lys Gln Glu His Arg Ile Gly Gly Tyr Lys Val Arg
                200                 205                 210

Asn Gln His Trp Ser Leu Ile Met Glu Ser Val Val Pro Ser Asp
                215                 220                 225

Lys Gly Asn Tyr Thr Cys Val Val Glu Asn Glu Tyr Gly Ser Ile
                230                 235                 240

Asn His Thr Tyr His Leu Asp Val Val Glu Arg Ser Pro His Arg
                245                 250                 255

Pro Ile Leu Gln Ala Gly Leu Pro Ala Asn Ala Ser Thr Val Val
                260                 265                 270

Gly Gly Asp Val Glu Phe Val Cys Lys Val Tyr Ser Asp Ala Gln
                275                 280                 285

Pro His Ile Gln Trp Ile Lys His Val Glu Lys Asn Gly Ser Lys
                290                 295                 300

Tyr Gly Pro Asp Gly Leu Pro Tyr Leu Lys Val Leu Lys Ala Ala
                305                 310                 315

Gly Val Asn Thr Thr Asp Lys Glu Ile Glu Val Leu Tyr Ile Arg
                320                 325                 330
```

```
Asn Val Thr Phe Glu Asp Ala Gly Glu Tyr Thr Cys Leu Ala Gly
                335                 340                 345

Asn Ser Ile Gly Ile Ser Phe His Ser Ala Trp Leu Thr Val Leu
                350                 355                 360

Pro Ala Pro Gly Arg Glu Lys Glu Ile Thr Ala Ser Pro Asp Tyr
                365                 370                 375

Leu Glu Ile Ala Ile Tyr Cys Ile Gly Val Phe Leu Ile Ala Cys
                380                 385                 390

Met Val Val Thr Val Ile Leu Cys Arg Met Lys Asn Thr Thr Lys
                395                 400                 405

Lys Pro Asp Phe Ser Ser Gln Pro Ala Val His Lys Leu Thr Lys
                410                 415                 420

Arg Ile Pro Leu Arg Arg Gln Val Thr Val Ser Ala Glu Ser Ser
                425                 430                 435

Ser Ser Met Asn Ser Asn Thr Pro Leu Val Arg Ile Thr Thr Arg
                440                 445                 450

Leu Ser Ser Thr Ala Asp Thr Pro Met Leu Ala Gly Val Ser Glu
                455                 460                 465

Tyr Glu Leu Pro Glu Asp Pro Lys Trp Glu Phe Pro Arg Asp Lys
                470                 475                 480

Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu
                500                 505                 510

Ala Val Thr Val Ala Val Lys Met Leu Lys Asp Asp Ala Thr Glu
                515                 520                 525

Lys Asp Leu Ser Asp Leu Val Ser Glu Met Glu Met Met Lys Met
                530                 535                 540

Ile Gly Lys His Lys Asn Ile Ile Asn Leu Leu Gly Ala Cys Thr
                545                 550                 555

Gln Asp Gly Pro Leu Tyr Val Ile Val Glu Tyr Ala Ser Lys Gly
                560                 565                 570

Asn Leu Arg Glu Tyr Leu Arg Ala Arg Arg Pro Pro Gly Met Glu
                575                 580                 585

Tyr Ser Tyr Asp Ile Asn Arg Val Pro Glu Glu Gln Met Thr Phe
                590                 595                 600

Lys Asp Leu Val Ser Cys Thr Tyr Gln Leu Ala Arg Gly Met Glu
                605                 610                 615

Tyr Leu Ala Ser Gln Lys Cys Ile His Arg Asp Leu Ala Ala Arg
                620                 625                 630

Asn Val Leu Val Thr Glu Asn Asn Val Met Lys Ile Ala Asp Phe
                635                 640                 645

Gly Leu Ala Arg Asp Ile Asn Asn Ile Asp Tyr Tyr Lys Lys Thr
                650                 655                 660

Thr Asn Gly Arg Leu Pro Val Lys Trp Met Ala Pro Glu Ala Leu
                665                 670                 675

Phe Asp Arg Val Tyr Thr His Gln Ser Asp Val Trp Ser Phe Gly
                680                 685                 690

Val Leu Met Trp Glu Ile Phe Thr Leu Gly Gly Ser Pro Tyr Pro
                695                 700                 705

Gly Ile Pro Val Glu Glu Leu Phe Lys Leu Leu Lys Glu Gly His
                710                 715                 720
```

```
Arg Met Asp Lys Pro Ala Asn Cys Thr Asn Glu Leu Tyr Met Met
            725                 730                 735

Met Arg Asp Cys Trp His Ala Val Pro Ser Gln Arg Pro Thr Phe
            740                 745                 750

Lys Gln Leu Val Glu Asp Leu Asp Arg Ile Leu Thr Leu Thr Thr
            755                 760                 765

Asn Glu Glu Tyr Leu Asp Leu Ser Gln Pro Leu Glu Gln Tyr Ser
            770                 775                 780

Pro Ser Tyr Pro Asp Thr Arg Ser Ser Cys Ser Ser Gly Asp Asp
            785                 790                 795

Ser Val Phe Ser Pro Asp Pro Met Pro Tyr Glu Pro Cys Leu Pro
            800                 805                 810

Gln Tyr Pro His Ile Asn Gly Ser Val Lys Thr
            815                 820

<210> SEQ ID NO 2
<211> LENGTH: 822
<212> TYPE: PRT
<213> ORGANISM: Homo sapiens

<400> SEQUENCE: 2

Met Val Ser Trp Gly Arg Phe Ile Cys Leu Val Val Thr Met
 1               5                  10                 15

Ala Thr Leu Ser Leu Ala Arg Pro Ser Phe Ser Leu Val Glu Asp
            20                  25                  30

Thr Thr Leu Glu Pro Glu Glu Pro Pro Thr Lys Tyr Gln Ile Ser
            35                  40                  45

Gln Pro Glu Val Tyr Val Ala Ala Pro Gly Glu Ser Leu Glu Val
            50                  55                  60

Arg Cys Leu Leu Lys Asp Ala Ala Val Ile Ser Trp Thr Lys Asp
            65                  70                  75

Gly Val His Leu Gly Pro Asn Asn Arg Thr Val Leu Ile Gly Glu
            80                  85                  90

Tyr Leu Gln Ile Lys Gly Ala Thr Pro Arg Asp Ser Gly Leu Tyr
            95                  100                 105

Ala Cys Thr Ala Ser Arg Thr Val Asp Ser Glu Thr Trp Tyr Phe
            110                 115                 120

Met Val Asn Val Thr Asp Ala Ile Ser Ser Gly Asp Asp Glu Asp
            125                 130                 135

Asp Thr Asp Gly Ala Glu Asp Phe Val Ser Glu Asn Ser Asn Asn
            140                 145                 150

Lys Arg Ala Pro Tyr Trp Thr Asn Thr Glu Lys Met Glu Lys Arg
            155                 160                 165

Leu His Ala Val Pro Ala Ala Asn Thr Val Lys Phe Arg Cys Pro
            170                 175                 180

Ala Gly Gly Asn Pro Met Pro Thr Met Arg Trp Leu Lys Asn Gly
            185                 190                 195

Lys Glu Phe Lys Gln Glu His Arg Ile Gly Gly Tyr Lys Val Arg
            200                 205                 210

Asn Gln His Trp Ser Leu Ile Met Glu Ser Val Val Pro Ser Asp
            215                 220                 225

Lys Gly Asn Tyr Thr Cys Val Val Glu Asn Glu Tyr Gly Ser Ile
            230                 235                 240

Asn His Thr Tyr His Leu Asp Val Val Glu Arg Ser Pro His Arg
            245                 250                 255
```

```
Pro Ile Leu Gln Ala Gly Leu Pro Ala Asn Ala Ser Thr Val Val
            260                 265                 270

Gly Gly Asp Val Glu Phe Val Cys Lys Val Tyr Ser Asp Ala Gln
        275                 280                 285

Pro His Ile Gln Trp Ile Lys His Val Glu Lys Asn Gly Ser Lys
    290                 295                 300

Tyr Gly Pro Asp Gly Leu Pro Tyr Leu Lys Val Leu Lys His Ser
305                 310                 315

Gly Ile Asn Ser Ser Asn Ala Glu Val Leu Ala Leu Phe Asn Val
            320                 325                 330

Thr Glu Ala Asp Ala Gly Glu Tyr Ile Cys Lys Val Ser Asn Tyr
        335                 340                 345

Ile Gly Gln Ala Asn Gln Ser Ala Trp Leu Thr Val Leu Pro Lys
    350                 355                 360

Gln Gln Ala Pro Gly Arg Glu Lys Glu Ile Thr Ala Ser Pro Asp
365                 370                 375

Tyr Leu Glu Ile Ala Ile Tyr Cys Ile Gly Val Phe Leu Ile Ala
            380                 385                 390

Cys Met Val Val Thr Val Ile Leu Cys Arg Met Lys Asn Thr Thr
        395                 400                 405

Lys Lys Pro Asp Phe Ser Ser Gln Pro Ala Val His Lys Leu Thr
    410                 415                 420

Lys Arg Ile Pro Leu Arg Arg Gln Val Thr Val Ser Ala Glu Ser
425                 430                 435

Ser Ser Ser Met Asn Ser Asn Thr Pro Leu Val Arg Ile Thr Thr
            440                 445                 450

Arg Leu Ser Ser Thr Ala Asp Thr Pro Met Leu Ala Gly Val Ser
        455                 460                 465

Glu Tyr Glu Leu Pro Glu Asp Pro Lys Trp Glu Phe Pro Arg Asp
    470                 475                 480

Lys Leu Thr Leu Gly Lys Pro Leu Gly Glu Gly Cys Phe Gly Gln
485                 490                 495

Val Val Met Ala Glu Ala Val Gly Ile Asp Lys Asp Lys Pro Lys
            500                 505                 510

Glu Ala Val Thr Val Ala Val Lys Met Leu Lys Asp Asp Ala Thr
        515                 520                 525

Glu Lys Asp Leu Ser Asp Leu Val Ser Glu Met Glu Met Met Lys
    530                 535                 540

Met Ile Gly Lys His Lys Asn Ile Ile Asn Leu Leu Gly Ala Cys
545                 550                 555

Thr Gln Asp Gly Pro Leu Tyr Val Ile Val Glu Tyr Ala Ser Lys
            560                 565                 570

Gly Asn Leu Arg Glu Tyr Leu Arg Ala Arg Arg Pro Pro Gly Met
        575                 580                 585

Glu Tyr Ser Tyr Asp Ile Asn Arg Val Pro Glu Glu Gln Met Thr
    590                 595                 600

Phe Lys Asp Leu Val Ser Cys Thr Tyr Gln Leu Ala Arg Arg Met
605                 610                 615

Glu Tyr Leu Ala Ser Gln Lys Cys Ile His Arg Asp Leu Ala Ala
            620                 625                 630

Arg Asn Val Leu Val Thr Glu Asn Asn Val Met Lys Ile Ala Asp
        635                 640                 645
```

-continued

```
Phe Gly Leu Ala Arg Asp Ile Asn Asn Ile Asp Tyr Tyr Lys Lys
                650                 655                 660
Thr Thr Asn Gly Arg Leu Pro Val Lys Trp Met Ala Pro Glu Ala
                665                 670                 675
Leu Phe Asp Arg Val Tyr Thr His Gln Ser Asp Val Trp Ser Phe
                680                 685                 690
Gly Val Leu Met Trp Glu Ile Phe Thr Leu Gly Gly Ser Pro Tyr
                695                 700                 705
Pro Gly Ile Pro Val Glu Glu Leu Phe Lys Leu Leu Lys Glu Gly
                710                 715                 720
His Arg Met Asp Lys Pro Ala Asn Cys Thr Asn Glu Leu Tyr Met
                725                 730                 735
Met Met Arg Asp Cys Trp His Ala Val Pro Ser Gln Arg Pro Thr
                740                 745                 750
Phe Lys Gln Leu Val Glu Asp Leu Asp Arg Ile Leu Thr Leu Thr
                755                 760                 765
Thr Asn Glu Glu Tyr Leu Asp Leu Ser Gln Pro Leu Glu Gln Tyr
                770                 775                 780
Ser Pro Ser Tyr Pro Asp Thr Arg Ser Ser Cys Ser Ser Gly Asp
                785                 790                 795
Asp Ser Val Phe Ser Pro Asp Pro Met Pro Tyr Glu Pro Cys Leu
                800                 805                 810
Pro Gln Tyr Pro His Ile Asn Gly Ser Val Lys Thr
                815                 820
```